(12) United States Patent
Mizukami (10) Patent No.: US 11,137,326 B2
(45) Date of Patent: *Oct. 5, 2021

(54) METHOD FOR EXTRACTING METAL COMPOUND PARTICLES, METHOD FOR ANALYZING THE METAL COMPOUND PARTICLES, AND ELECTROLYTIC SOLUTION USED THEREFOR

(71) Applicant: NIPPON STEEL & SUMITOMO METAL CORPORATION, Tokyo (JP)

(72) Inventor: Kazumi Mizukami, Tokyo (JP)

(73) Assignee: NIPPON STEEL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/999,826

(22) PCT Filed: Feb. 17, 2017

(86) PCT No.: PCT/JP2017/006001
§ 371 (c)(1),
(2) Date: Aug. 20, 2018

(87) PCT Pub. No.: WO2017/142088
PCT Pub. Date: Aug. 24, 2017

(65) Prior Publication Data
US 2020/0141023 A1    May 7, 2020

(30) Foreign Application Priority Data
Feb. 18, 2016 (JP) .............................. JP2016-028849

(51) Int. Cl.
*C25F 3/02* (2006.01)
*C25F 3/06* (2006.01)
(Continued)

(52) U.S. Cl.
CPC ................ *G01N 1/32* (2013.01); *C25F 3/02* (2013.01); *C25F 3/06* (2013.01); *G01N 33/2028* (2019.01)

(58) Field of Classification Search
CPC ...................................................... G01N 1/32
See application file for complete search history.

(56) References Cited

U.S. PATENT DOCUMENTS 4,111,767 A      9/1978 Kawagishi et al.
2002/0108861 A1*  8/2002 Emesh ................ H01L 21/7684
                                                     205/81

(Continued)

FOREIGN PATENT DOCUMENTS

CN    101688857 A    3/2010
CN    102213654 A    10/2011
(Continued)

OTHER PUBLICATIONS

Author unknown, "Steel Handbook", Oct. 30, 1981, pp. 332-333 (4 pages).

(Continued)

*Primary Examiner* — Brian W Cohen
(74) *Attorney, Agent, or Firm* — Birch, Stewart, Kolasch & Birch, LLP (57) ABSTRACT

The object of the present invention is such that a surface exchange of metal fine particles by Cu ions, or the like is inhibited in order to prevent formation of Artificial CuS or the like, in extraction and analysis of the metal fine particles (inclusions and precipitates) in a metal material by electrolytic corrosion in a solvent-based electrolytic solution, without significantly changing conventional extraction and analysis methods.

(Continued)

A method for extracting metal compound particles in a metal material by etching the metal material in an electrolytic solution, characterized by using the following electrolytic solution,
wherein it comprises a chemical agent that forms a complex containing metal M' wherein Δ defined by the following formula is 10 or more, $$\Delta = pKsp[M'x'Ay'] - pKsp[MxAy]$$
$$= (-\log_{10}Ksp[M'x'Ay']) - (-\log_{10}Ksp[MxAy])$$

wherein a solubility product of metal compound M'x'Ay' is defined as Ksp[M'x'Ay'], and a solubility product of metal compound to be extracted MxAy, which is contained in the metal material, is defined as Ksp[MxAy], as well as the electrolytic solution therefor.

9 Claims, 7 Drawing Sheets

(51) Int. Cl.
  G01N 1/32 (2006.01)
  G01N 33/2028 (2019.01)

(56) References Cited

U.S. PATENT DOCUMENTS

| | | | |
|---|---|---|---|
| 2005/0230354 A1* | 10/2005 | Hardikar | C11D 3/044 216/88 |
| 2006/0006074 A1 | 1/2006 | Liu et al. | |
| 2007/0062408 A1 | 3/2007 | Chen et al. | |
| 2009/0139875 A1 | 6/2009 | Kim et al. | |
| 2010/0178767 A1* | 7/2010 | Schubert | H01L 21/3212 438/692 |
| 2010/0291692 A1 | 11/2010 | Kinoshiro et al. | |
| 2013/0004389 A1 | 1/2013 | Okamoto et al. | |
| 2014/0131080 A1 | 5/2014 | Hirao et al. | |
| 2020/0141843 A1* | 5/2020 | Mizukami | C25F 7/00 |

FOREIGN PATENT DOCUMENTS

| | | |
|---|---|---|
| CN | 102538703 A | 7/2012 |
| CN | 102818723 A | 12/2012 |
| GB | 892054 A | 3/1962 |
| JP | 51-78392 A | 7/1976 |
| JP | 54-79131 A | 6/1979 |
| JP | 59-141035 A | 8/1984 |
| JP | 62-238379 A | 10/1987 |
| JP | 6-118050 A | 4/1994 |
| JP | 2000-137015 A | 5/2000 |
| JP | 2002-303620 A | 10/2002 |
| JP | 2002-363713 A | 12/2002 |
| JP | 2004-317203 A | 11/2004 |
| JP | 2009-31269 A | 2/2009 |
| JP | 2009-509050 A | 3/2009 |
| JP | 2009-131949 A | 6/2009 |
| JP | 2010-127792 A | 6/2010 |
| JP | 2011-156521 A | 8/2011 |
| JP | 2013-107381 A | 6/2013 |
| JP | 5550933 B2 | 7/2014 |
| JP | 2015-52589 A | 3/2015 |
| KR | 10-1163299 B | 7/2012 |
| SU | 597966 A1 | 3/1978 |
| SU | 643552 A1 | 1/1979 |

OTHER PUBLICATIONS

Author unknown, Japan Chemical Journal, vol. 88, No. 11, 1967, pp. 1168-1171(4 pages).
Hamada et al., "$Cu^{2+}$-Citrate Dimer Complexes in Aqueous Solutions", Journal of Basic & Applied Sciences, vol. 1, 2015, pp. 583-585(3 pages).
Japanese Information Statement, dated Jun. 12, 2019, for Japanese Application No. 2018-500237, with an English translation.
Tan et al., "Formation of Copper Sulfide Artifacts During Electrolytic Dissolution of Steel", Metallurgical and Materials Transactions B, vol. 44B, Jun. 2013, pp. 483-486 (4 pages).
Tominaga et al., "Synthesis of Fine Copper Particles by Reduction of Copper Acetylacetonato Chelate Complex", Color Material, vol. 65, No. 3, 1992, pp. 149-154 (6 pages, with abstract.).
Yoshimura et al., "Conditions for Crystallization of Various Copper(II) Complexes of Salicylic Acid in Aqueous Solution", Journal of the Chemical Society of Japan, No. 4, 1979, pp. 502-505 (4 pages with abstract.).
Taiwanese Office Action and Search Report, dated Oct. 5, 2017, for corresponding Taiwanese Application No. 106105330.
Russian Office Action and Search Report, dated Apr. 5, 2019, for corresponding Russian Application No. 201832863/05(053828), with an English translation.
Chinese Office Action dated Feb. 3, 2020, for corresponding Chinese Application No. 201780003434.9, with English translation.
Author unknown, "Chemistry Handbook 5th Edition", Basic II, The Chemical Society of Japan, Feb. 20, 2004, Front cover page, index and pp. 352-354 (8 pages total).
Author unknown, "Chemistry Handbook", Advanced, Nov. 20, 1965, Front cover page, p. 1259, index xvii and back cover page (4 pages total).
Author unknown, "Dictionary of Physical and Chemical Science, 5th Edition". Feb. 20, 1998, Front cover page, pp. 58-59 and Back cover page (4 pages total).
Kurosawa et al., "Observation and Analysis of Sulfides in Steels Using Non-Aqueous Electrolyte-Potentiostatic Etching Method", Journal of Japan Metallurgy Society, vol. 44, 1980, pp. 677-686 with an English abstract.
Steinberg, "Stability of Metal Complexes with Salicylic Acid and Related Substances", Nature, vol. 162, No. 4637, Sep. 13, 1958, pp. 741-742.
Wakamatsu, "A New Anodic Dissolution Technique for the isolation of Precipitates and Inclusions from Steel", Iron and Steel, No. 14, 1969, pp. 65-75, with an English abstract.
Korean Office Action, dated Apr. 24, 2020, for corresponding Korean Application No. 10-2018-7010330, along with an English translation.
Abe, "Solubility Products and Electronegativity of Metal Sulfides" Chemical Education, vol. 26, No. 2, 1978, pp. 188-190, 3 pages total.
Kojima et al., "Focusing chromatography using precipitation reagent; The relation between solubility products and migration distance of sulfide and hydroxide of group II, III metals" Analytical Chemistry, vol. 31, 1982, pp. 125-129, 5 pages total.
Extended European Search Report dated Sep. 3, 2019, for European Patent Application No. 17753342.9.
Japanese Office Action, dated Jun. 25, 2019, for Japanese Application No. 2018-500237, with an English translation.
Kurosawa et al., "Observation and Analysis of Sulfides in Steels Using Non-Aqueous Electrolyte-Potentiostatic Etching Method", Journal of Japan Institute of Metals and Materials, vol. 6, No. 44, 1980, pp. 677-686 (10 pages with abstract).

\* cited by examiner

Table 1: The solubility products of the sulfides in an aqueous solution at 25°C and the pKsp difference Δ of the sulfides.

| No | Compound | Formula | $K_{sp}$ (at 25°C) | $pK_{sp}$ | HgS | Ag₂S | CuS | PbS | CdS | NiS | ZnS | CoS | Tl₂S | FeS |
|---|---|---|---|---|---|---|---|---|---|---|---|---|---|---|
| 1 | Mercury(II) sulfide (red) | HgS | $2 \times 10^{-54}$ | 53.7 | | | | | | | | | | |
| 2 | Silver(I) sulfide | Ag₂S | $8 \times 10^{-51}$ | 50.1 | 3.7 | | | | | | | | | |
| 3 | Copper(II) sulfide | CuS | $8 \times 10^{-37}$ | 36.1 | 17.6 | 14.0 | | | | | | | | |
| 4 | Lead(II) sulfide | PbS | $3 \times 10^{-28}$ | 27.5 | 26.2 | 22.6 | 8.6 | | | | | | | |
| 5 | Cadmium sulfide | CdS | $1 \times 10^{-27}$ | 27.0 | 26.7 | 23.1 | 9.1 | 0.5 | | | | | | |
| 6 | Nickel(II) sulfide (beta) | NiS | $1.3 \times 10^{-25}$ | 24.9 | 28.8 | 25.2 | 11.2 | 2.6 | 2.1 | | | | | |
| 7 | Zinc sulfide (alpha) | ZnS | $2 \times 10^{-25}$ | 24.7 | 29.0 | 25.4 | 11.4 | 2.8 | 2.3 | 0.2 | | | | |
| 8 | Cobalt(II) sulfide (beta) | CoS | $3 \times 10^{-26}$ | 24.5 | 29.2 | 25.6 | 11.6 | 3.0 | 2.5 | 0.4 | 0.2 | | | |
| 9 | Thallium(I) sulfide | Tl₂S | $6 \times 10^{-22}$ | 21.2 | 32.5 | 28.9 | 14.9 | 6.3 | 5.8 | 3.7 | 3.5 | 3.3 | | |
| 10 | Iron(II) sulfide | FeS | $8 \times 10^{-19}$ | 18.1 | 35.6 | 32.0 | 18.0 | 9.4 | 8.9 | 6.8 | 6.6 | 6.4 | 3.1 | 0.0 |
| 11 | Manganese(II) sulfide (green) | MnS | $3 \times 10^{-14}$ | 13.5 | 40.2 | 36.6 | 22.6 | 14.0 | 13.5 | 11.4 | 11.2 | 11.0 | 7.7 | 4.6 |

☐ Combination in which the pKsp difference Δ is 22 or more (CuS vs MnS) (Expecting degree of exchange reaction √√)

☐ The pKsp difference Δ is 10 or more and less than 22, and ion exchange reaction is expected (√√ to √)

☐ The pKsp difference Δ is less than 10, and expecting degree of ion exchange reaction is low (√ to -)

FIG. 7

Table 4: the pKsp difference Δ of the selenides in an aqueous solution at 25°C.

| No | Compound | Formula | $K_{sp}$ (at 25°C) | pK$_{sp}$ | HgSe | Ag$_2$Se | CuSe | PbSe | CdSe | Tl$_2$Se | NiSe | CoSe | ZnSe | FeSe |
|---|---|---|---|---|---|---|---|---|---|---|---|---|---|---|
| | | | | | 64.5 | 63.7 | 48.1 | 42.1 | 35.2 | 33.1 | 32.7 | 31.2 | 29.4 | 22 |
| 1 | Mercury(II) selenide | HgSe | | 64.5 | | | | | | | | | | |
| 2 | Silver(I) selenide | Ag$_2$Se | | 63.7 | 0.8 | 0 | | | | | | | | |
| 3 | Copper(II) selenide | CuSe | | 48.1 | 16.4 | 15.6 | 0 | | | | | | | |
| 4 | Lead(II) selenide | PbSe | | 42.1 | 22.4 | 21.6 | 6 | 0 | | | | | | |
| 5 | Cadmium selenide | CdSe | | 35.2 | 29.3 | 28.5 | 12.9 | 6.9 | 0 | | | | | |
| 6 | Thallium(I) selenide | Tl$_2$Se | | 33.1 | 31.4 | 30.6 | 15 | 9 | 2.1 | 0 | | | | |
| 7 | Nickel(II) selenide | NiSe | | 32.7 | 31.8 | 31 | 15.4 | 9.4 | 2.5 | 0.4 | 0 | | | |
| 8 | Cobalt(II) selenide | CoSe | | 31.2 | 33.3 | 32.5 | 16.9 | 10.9 | 4 | 1.9 | 1.5 | 0 | | |
| 9 | Zinc selenide | ZnSe | | 29.4 | 35.1 | 34.3 | 18.7 | 12.7 | 5.8 | 3.7 | 3.3 | 1.8 | 0 | |
| 10 | Iron(II) selenide | FeSe | | 22 | 42.5 | 41.7 | 26.1 | 20.1 | 13.2 | 11.1 | 10.7 | 9.2 | 7.4 | 0 |
| 11 | Manganese(II) selenide | MnSe | | 11.5 | 53 | 52.2 | 36.6 | 30.6 | 23.7 | 21.6 | 21.2 | 19.7 | 17.9 | 10.5 |

☐ Combination in which the pKsp difference Δ is 22 or more (CuSe vs MnSe) (Expecting degree of exchange reaction √√)

☐ The pKsp difference Δ is 10 or more and less than 22, and ion exchange reaction is expected (√√ to √)

☐ The pKsp difference Δ is less than 10, and expecting degree of ion exchange reaction is low (√ to ×)

METHOD FOR EXTRACTING METAL COMPOUND PARTICLES, METHOD FOR ANALYZING THE METAL COMPOUND PARTICLES, AND ELECTROLYTIC SOLUTION USED THEREFOR

FIELD

The present invention relates to a method for extracting metal compound particles using an electrolytic solution containing a chemical agent for trapping a specific metal when a metal material is etched in the electrolytic solution to extract metal compound particles in the metal material, a method for analyzing the metal compound particles, and an electrolytic solution therefor.

BACKGROUND

It is widely practiced to control strengths and characteristics of metal materials, in particular, steel materials to the required level by controlling types of inclusions and precipitates present in the material matrix, their shapes such as aspect ratios and their dimensions, as a result of trace amounts of added elements and various heat treatments.

Therefore, observation of inclusions and/or precipitates, and measurement of components and amounts thereof have important meanings in quality control of steel materials and analysis of manufacturing processes.

In order to observe inclusions and precipitates by SEM or the like, it is necessary to expose the inclusions and precipitates buried in the matrix to the observation surface. Conventionally, the inclusions and precipitates are exposed to the surface of sample to make it observable by electrolytic dissolution of the sample in various electrolyte solutions.

In recent years, due to the progress of the manufacturing technology of steel materials, the types of inclusions and precipitates are diversified, and they are finely dispersed. For their observation, it is required for an electrolyte solution to selectively dissolve only the matrix (Fe), but not to dissolve inclusions and precipitates, even if they are fine grains, so that the inclusions and precipitates would surely retain on the observation surface.

In addition, when identifying and quantitatively analyzing these inclusions and precipitates, the matrix of the steel sample is dissolved in the electrolyte solution, and phases are collected as an electrolytic residue to carry out their identification and quantitative analysis.

In the case of this quantitative analysis, it is necessary that only the matrix portion of the steel material is efficiently electrolyzed, the Fe component is reliably dissolved to be retained in the electrolytic solution, and the other portion corresponding to inclusions and precipitates is surely recovered as an electrolytic residue.

Patent Document 1 describes an electrolytic solution composition for a steel sample, and a method for analyzing inclusions and precipitates using the same.

On the contrary that many of the conventional electrolytic solutions were acidic, this electrolytic solution composition comprises an added alkaline triethanolamine. As a result, particles of the inclusions and precipitates are rarely dissolved and tend to remain on the surface of the steel material sample, even if the inclusions and precipitates are fine. Accordingly, after taking out the steel sample from the electrolytic solution and drying it, it is possible to observe and analyze the inclusions and precipitates as they are by SEM or the like.

In addition, Patent Document 2 discloses inventions relating to a nonaqueous solvent based electrolytic solution for extracting inclusions and precipitates in a steel sample and a method for electrolytically extracting a steel sample using the same.

This electrolytic solution contains maleic anhydride, tetramethylammonium chloride and methanol in a predetermined ratio, and is an electrolyte solution excellent in the ability to electrolyze a large amount of steel sample at a time. It is characterized in that maleic anhydride contained in the solution forms an iron complex and prevents formation of precipitate such as Fe hydroxide.

On the other hand, Patent Document 3 discloses a technology of use of triethylenetetramine (TETA) and ethylenediaminetetraacetic acid (EDTA) as an anti-floating agent for arsenic mineral, in order to precipitate and separate arsenic, i.e., an impurity element, with copper ions, in a copper-containing mineral, which technology does not relate to a steel sample.

In order to observe inclusions and precipitates in a steel sample in situ by SEM or the like, it is necessary to electrolyze the sample so that the matrix constituting Fe component is retained in the electrolytic solution with the Fe ion chelating agent and the inclusions and precipitates remain on the sample surface.

On the other hand, in the case of quantitative analysis of inclusions or precipitates, the Fe component of the matrix is retained in the electrolytic solution by a chelating agent, and by using an electrolytic solution which does not dissolve the inclusions and precipitates separated from the sample by electrolytic dissolution, the inclusions and precipitates are recovered as an electrolytic residue to identify and quantitatively analyze the residue.

Therefore, with regard to an electrolyte solution aiming for the collection of a residue for identification and quantitative analysis of inclusions and precipitates, the main focus is on maintaining Fe component in the dissolved state as chelate complex in the electrolytic solution. No particular consideration was given to contamination of the inclusions and the precipitates in the electrolytic solution.

PRIOR ART DOCUMENT

Patent Document

[PATENT DOCUMENT 1] Japanese Unexamined Patent Publication (Kokai) No. 2002-303620
[PATENT DOCUMENT 2] Japanese Unexamined Patent Publication (Kokai) No. 2000-137015
[PATENT DOCUMENT 3] Japanese Unexamined Patent Publication (Kokai) No. 2011-156521

SUMMARY

Disclosure of the Invention

In analyzing metal compounds in steel materials, for example, by electrolytic corrosion in a conventional non-aqueous solvent-based electrolytic solution, an unknown phenomenon that higher content of CuS is observed than that measured by means other than the electrolytic operation has sometimes been observed for fine particles of inclusions and precipitates, particularly of various metal compounds, especially on MnS surface layer. Accordingly, it is believed that MnS particles are detected as if it were CuS (Artificial CuS).

The inventors of the present invention have studied in detail the cause thereof. As a result, it was discovered that, when a metal ion having a small solubility product Ksp ($Cu^{2+}$) is produced in the electrolytic solution by an electrolytic operation, a metal ion having a large Ksp solubility product ($Mn^{2+}$) is exchanged with the metal ion having a small solubility product Ksp ($Cu^{2+}$) on the surface of the metal sulfide (MnS). It was also found that the exchange of metal ions on the sulfide surface would easily proceed at a normal temperature and a normal pressure even in an aqueous solution or a nonaqueous solvent.

As a result, inclusions and precipitates which originally existed as MnS in the steel sample were observed as CuS, when the surface of the sample was observed. Further, in the case of fine particles, where CuS derived from Cu ions in the electrolytic solution is exchanged with MnS to the depth of several tens of nm (1 to 100 nm) from the surface of MnS, a substantial portion of the volume of the fine particles will be occupied by CuS. Therefore, it became impossible to accurately quantify MnS, even if mass spectrometry is performed to a sample from the residue.

In the above description, although the case of attack on the MnS surface by Cu (exchange phenomenon of Mn atom by Cu atom on the MnS surface) was explained, it can be presumed that similar phenomena may occur for metals other than Cu. That is, it can be presumed that exchange of metal ions on the surface of the metal compound will easily proceed when there is a certain difference between a larger solubility product Ksp and a smaller solubility product Ksp (in order of 10 digits ($10^{10}$) or more). In the specification, this phenomenon is referred to as "Artifact." More specifically, when the difference in pKsp between two compounds having different solubility products Ksp (hereinafter sometimes referred to as Δ) is about 10 or more, it is estimated that an exchange between the compound having a larger pKsp (smaller solubility product Ksp) and the compound having a smaller pKsp (larger solubility product) will easily proceed.

The above condition can be expressed by the following equation.

$$\Delta = pKsp[\text{compound(smaller } Ksp)] - pKsp[\text{compound (larger } Ksp)] = (-\log_{10} Ksp[\text{compound(smaller } Ksp)]) - (-\log_{10} Ksp[\text{compound(larger } Ksp)]) \geq 10,$$

where, the solubility product Ksp of a certain compound is expressed as Ksp [compound], and pKsp [compound]=−$\log_{10}$ Ksp [compound].

In fact, it was confirmed that, when a simulation experiment in which Ag exerts on MnS was carried out by the inventors, Ag attacked MnS to ionize Mn and expel it into the electrolytic solution and Ag, itself remained as $Ag_2S$ on the surface of MnS. Comparing the solubility product (or pKsp) of $Ag_2S$ with that of MnS, $Ag_2S$ has a smaller solubility product Ksp (larger pKsp) and MnS has a larger solubility product Ksp (smaller pKsp). The difference in the solubility products Ksp between $Ag_2S$ and MnS is 37 digits, and the pKsp difference Δ is 36.6. It is expressed by the following equation.

$$\Delta = pKsp[Ag_2S] - pKsp[MnS] = 50.1 - 13.5 = 36.6 \geq 10$$

The problems to be solved by the present invention are as follows.

In the extraction and analysis of metal fine particles (inclusions and precipitates) in metal materials by electrolytic corrosion method or the like in a solvent-based electrolytic solution, formation of Artificial CuS and the like is prevented by inhibiting a surface exchange of the metal fine particles with Cu ions and the like.

Formation of Artificial CuS and the like is prevented particularly on metal sulfides (MnS, FeS etc.).

Means for Solving the Problem

The inventors of the present invention have conducted intensive studies on a strategy for solving the above-mentioned problems.

As a result, from the observation that an exchange phenomenon does not occur unless a metal that forms Artifact metal sulfide (referred to as "attack metal") is present in the solvent-based electrolytic solution, it was conceived that capturing such an attack metal would be effective. That is, it was conceived that, by adding a chemical agent (chelating agent or the like) that selectively captures a metal that forms Artifact metal sulfide (attack metal) into a solvent-based electrolytic solution, a free attack metal in the electrolytic solution will be reduced, and no Artifact metal sulfide will be produced.

For example, Cu ions dissolved from a steel sample or the like are retained in an electrolytic solution by a Cu ion chelating agent so as not to attack MnS on the surface of the steel sample for surface observation. Or, similarly Cu ions are retained in the electrolytic solution as a chelate complex with a Cu chelating agent, upon the electrolytic operation for identifying and quantifying inclusions and precipitates. Accordingly, CuS will not be incorporated into a residue for quantitative analysis made from inclusions and precipitates. As a result, it is possible to observe the inclusions and precipitates in the steel sample for surface observation as their original form. In addition, since the electrolytic residue for analysis does not contain CuS or the like derived from Cu ions dissolved from the matrix or the like of the sample, it is possible to precisely identify and quantify only the elements derived from the inclusions and precipitates contained in the original steel sample.

The present invention has been made on the basis of the above findings, and its summary is as follows.

(1) A method for extracting metal compound particles in a metal material by etching the metal material in an electrolytic solution, characterized by using the following electrolytic solution, wherein it comprises a chemical agent that forms a complex containing metal M' wherein Δ defined by the following formula is 10 or more, $$\Delta = pKsp[M'x'Ay'] - pKsp[MxAy] = (-\log_{10} Ksp[M'x'Ay']) - (-\log_{10} Ksp[MxAy])$$

wherein a solubility product of metal compound M'x'Ay' is defined as Ksp[M'x'Ay'], and a solubility product of metal compound to be extracted MxAy, which is contained in the metal material, is defined as Ksp[MxAy], and wherein M and M' are different metal elements, A is a single atom or atomic group forming a compound with M or M', and x, x', y and y' represent a composition ratio of the compound determined according to the valences of M, M' and A, and the solubility product Ksp is a value in an aqueous solution at 25° C.

(2) The method for extracting metal compound particles according to item (1) above, wherein the electrolytic solution is a nonaqueous solvent-based electrolytic solution.

(3) The method for extracting metal compound particles according to item (1) or (2) above, wherein the metal compound to be extracted MxAy is one or two of MnS and FeS.

(4) The method for extracting metal compound particles according to any one of items (1) to (3) above, wherein the metal M' of the metal compound M'x'Ay' is at least one of Hg, Ag, Cu, Pb, Cd, Co, Zn and Ni.

(5) The method for extracting metal compound particles according to any one of items (1) to (4) above, wherein the chemical agent comprises a crown ether.

(6) The method for extracting metal compound particles according to any one of items (1) to (5) above, wherein the chemical agent comprises any one kind or two or more kinds of polyethylene amines, ethylenediamine tetraacetic acid, cyclohexanediamine tetraacetic acid.

(7) The method for extracting metal compound particles according to item (6) above, wherein the chemical agent comprises triethylenetetramine.

(8) The method for extracting metal compound particles according to any one of items (1) to (7) above, wherein the metal material is a steel material.

(9) The method for extracting metal compound particles according to any one of items (1) to (8) above, wherein, when passing the electrolytic solution after etching through a filter and extracting metal compound particles as a collected residue, the filter is a tetrafluoroethylene resin filter.

(10) A method for analyzing metal compound particles characterized by analyzing the metal compound particles extracted by the method for extracting metal compound particles according to any one of items (1) to (9) above.

(11) An electrolytic solution used for extracting metal compound particles in a metal material by etching the metal material, wherein the electrolytic solution comprises a chemical agent that forms a complex containing metal M' wherein $\Delta$ defined by the following formula is 10 or more, $$\Delta = pKsp[M'x'Ay'] - pKsp[MxAy] = (-\log_{10} Ksp[M'x'Ay']) - (-\log_{10} Ksp[MxAy])$$

wherein a solubility product of metal compound M'x'Ay' is defined as Ksp[M'x'Ay'], and a solubility product of metal compound to be extracted MxAy contained in the metal material is defined as Ksp[MxAy], and
wherein M and M' are different metal elements, A is a single atom or atomic group forming a compound with M or M', and x, x', y and y' represent a composition ratio of the compound determined according to the valence of M, M' and A, and the solubility product Ksp is a value in an aqueous solution at 25° C.

(12) The electrolytic solution according to item (11) above, wherein it is a nonaqueous solvent system.

(13) The electrolytic solution according to item (11) or (12) above, wherein the metal compound to be extracted MxAy is one or two of MnS or FeS.

(14) The electrolytic solution according to any one of items (11) to (13) above, wherein the metal M' of the metal compound M'x'Ay' is at least one of Hg, Ag, Cu, Pb, Cd, Co, Zn and Ni.

(15) The electrolytic solution according to any one of items (11) to (14) above, wherein the chemical agent comprises a crown ether.

(16) The electrolytic solution according to any one of items (11) to (15) above, wherein the chemical agent comprises any one kind or two or more kinds of polyethylene amines, ethylenediamine tetraacetic acid, cyclohexanediamine tetraacetic acid.

(17) The electrolytic solution according to the item (16) above, wherein the chemical agent comprises triethylenetetramine.

(18) The electrolytic solution according to any one of items (11) to (17) above, wherein the metal material is a steel material.

(19) The electrolytic solution according to any one of items (11) to (18) above, wherein the nonaqueous solvent contains at least one of methanol and ethanol.

Effect of the Invention

According to the present invention, by analyzing the surface of the extracted metal fine particles, MnS or FeS fine particles are no longer misidentified as CuS, and the true appearance (size, component) of the metal sulfide can be known. In addition, the content of metal sulfide in the steel material can be accurately measured.

According to the present invention, it becomes possible that inclusions or precipitates and the like exposed on the surface of the steel sheet by electrolytic operation are observed as the same components and form originally present in the steel sample. Further, in a quantitative analysis of inclusions and precipitate components from the analysis of the electrolytic residue, it is possible to accurately perform a quantitative analysis without being influenced by Cu or the like incorporated from the electrolytic solution. Therefore, observation of the structure of the steel sample, and identification and quantitative analysis of the inclusions and precipitates can be greatly improved.

DESCRIPTION OF EMBODIMENTS

According to the present invention, there is provided a method for extracting metal compound particles in a metal material by etching the metal material in an electrolytic solution, characterized by using the following electrolytic solution, wherein it comprises a chemical agent that forms a complex containing metal M' wherein $\Delta$ defined by the following formula is 10 or more, $$\Delta = pKsp[M'x'Ay'] - pKsp[MxAy] = (-\log_{10} Ksp[M'x'Ay']) - (-\log_{10} Ksp[MxAy])$$

wherein a solubility product of metal compound M'x'Ay' is defined as Ksp[M'x'Ay'], and a solubility product of metal compound to be extracted MxAy contained in the metal material is defined as Ksp[MxAy], and wherein M and M' are different metal elements, A is a single atom or atomic group forming a compound with M or M', and x, x', y and y' represent a composition ratio of the compound determined according to the valences of M, M' and A, and the solubility product Ksp is a value in an aqueous solution at 25° C.

In the present invention, metal compound particles in the metal material are extracted. That is, by etching the metal material in the electrolytic solution, a matrix (Fe or the like) is selectively dissolved to expose metal compound particles such as inclusions and precipitates contained in the metal material onto the sample surface. This makes it possible to observe the metal compound particles.

As a method for extracting fine particles in a metal sample, for example, an acid decomposition method of dissolving an iron matrix of a steel sample in an acid solution, a halogen dissolution method wherein an iron matrix of a steel sample is dissolved in a iodine/methanol mixed solution or a bromine/methanol mixed solution, a nonaqueous solvent constant current electrolytic dissolution method and a nonaqueous solvent-based potentiostatic electrolytic method (SPEED: Selective Potentiostatic Etching by Electrolytic Dissolution Method), or the like can be used. Among them, SPEED method using a nonaqueous solvent is preferable because a change in composition and size rarely occurs when fine particles are dispersed in a solvent, and thus even unstable fine particles can be stably extracted. With respect to the present embodiment, an explanation will be given by taking an evaluation method of fine particles in a steel material by Selective Potentiostatic Etching by Electrolytic Dissolution Method (SPEED method) with reference to FIG. 1. However, the extraction method in the present invention is not limited to SPEED method, and the metal material is not limited to a steel material.

Figure 1:
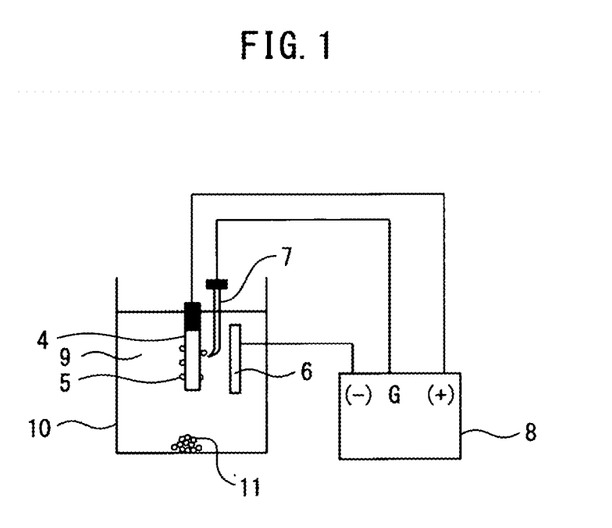
FIG. 1 shows an example of a sketch of an electrolytic apparatus using an electrolyte solution according to the present invention.

Initially, the metal sample 4 is processed to a size of, for example, 20 mm×40 mm×2 mm, an oxide film such as a scale on the surface layer is removed by chemical polishing or mechanical polishing or the like to reveal a metal layer. Conversely, when analyzing microparticles contained in the oxide film layer, the surface layer should be left as it is.

Next, this metal sample is electrolyzed by using SPEED method. Specifically, the electrolytic solution 9 is filled in the electrolytic bath 10, the metal sample 4 is immersed in the electrolytic solution 9, and the reference electrode 7 is brought into contact with the metal sample 4. The platinum electrode 6 and the metal sample 4 are connected to the electrolytic apparatus 8. Generally, when the above electrolytic method is used, the electrolytic potential of fine particles such as precipitates in the steel is higher than that of the metal portion being a matrix of the metal sample 4. Therefore, it is possible to selectively dissolve only the matrix by setting an electrolytic potential using the electrolytic apparatus 8 at which the matrix of the metal sample 4 is dissolved and fine particles such as precipitates are not dissolved.

The inclusions or the precipitates 5 emerge on the surface of the sample where Fe in the surface matrix portion is electrolytically eluted, and become suitable for observation by SEM or the like. Further, electrolytic dissolution may be continued to separate the inclusions or precipitates from the surface of the sample to recover them as the electrolytic residue 11 by filtrating and separating them from the electrolytic solution, and then the residue 11 may be subjected to identification and quantitative analysis.

An electrolytic solution for the metal material according to the present invention, that is, an electrolytic solution to electrolyze the surface Fe matrix for observation of the inclusions and precipitates, to electrolyze the Fe matrix for quantitative analysis of the inclusions and precipitates, and to be used for electrolytic dissolution for recovering the residue preferably comprises, (1) a complex forming agent for Fe ions,
(2) an electrolyte for ensuring conductivity in the electrolytic solution, and
(3) a solvent for retaining the formed complex such as Fe complex in the solution.

As the complex forming agent for Fe ions, one or more of acetylacetone, maleic anhydride, maleic acid, triethanolamine, salicylic acid and methyl salicylate may be selected.

As the electrolyte, one or more of tetramethylammonium chloride (TMAC), sodium chloride (NaCl) and lithium chloride (LiCl) can be selected.

The solvent needs to be capable of retaining various complex forming agents and complexes of the complex forming agent and Fe in a dissolved state, and may be a nonaqueous solvent. In the aqueous electrolytic solution, various precipitates are decomposed even at relatively low electrolytic dissolution voltage (for example, −300 mV or less), whereas the nonaqueous solvent-based electrolytic solution has a wide stable electrolytic dissolution region and can be applied to almost all steel materials from superalloy, high alloy, stainless steel to carbon steel. When a nonaqueous solvent-based electrolytic solution is used, only dissolution of the matrix and (complexation) reaction of the dissolved Fe ion and the chelating agent occur, and the inclusions or precipitates 5 do not dissolve. Accordingly, "in situ" state three-dimensional observation and analysis on the base material can be performed. As the nonaqueous solvent, a compound which promotes electrolytic dissolution smoothly and dissolves a complexable organic compound and a carrier electrolyte is suitable. For example, a lower alcohol such as methanol, ethanol or isopropyl alcohol may be used. Methanol, ethanol or a mixture thereof may be selected. Further, solvents having a polarity (dipole moment or the like) equal to or higher than those of these alcohols can be used.

In the conventional constant potential electrolytic dissolution method, for example, a 10% by mass of acetylacetone (hereinafter referred to as "AA")-1% by mass of tetramethylammonium chloride (hereinafter referred to as "TMAC")-methanol solution, or a 10% by mass of maleic anhydride-2% by mass of TMAC-methanol solution is used as an electrolytic solution. These electrolytic solutions are frequently used because an electrolytically eluted Fe preferably forms a complex and the produced Fe complex is dissolved in the electrolytic solution.

Metals other than the matrix (Fe) may be eluted in the electrolytic solution even though the amount thereof is relatively small as compared with the matrix (Fe). The inventors found that, when the eluted metal has a small solubility product Ksp (in other words, a high pKsp(=$\log_{10}$ Ksp)) and the inclusions or precipitates 5, or the electrolytic residue 11 contain a metal compound of which metal has a large solubility product Ksp (pKsp is small), a metal ion having a large solubility product Ksp (pKsp is small) (for example, $Mn^{2+}$) is exchanged with a metal ion having a small solubility product Ksp (large pKsp) (for example, $Cu^{2+}$) on the surface of the metal compound. It is considered that, when the difference in solubility products Ksp is greater than or equal to 10 digits ($10^{10}$) or more, or more specifically, when the pKsp difference Δ of two compounds having different solubility products Ksp is about 10 or more, the exchange of the metal ions will progress easily. It is considered that, when the difference in solubility product Ksp is greater than 20 digits ($10^{20}$) or more, or more specifically, when the pKsp difference Δ is about 20 or more, the exchange of the metal ions will proceed more easily.

Figure 6:
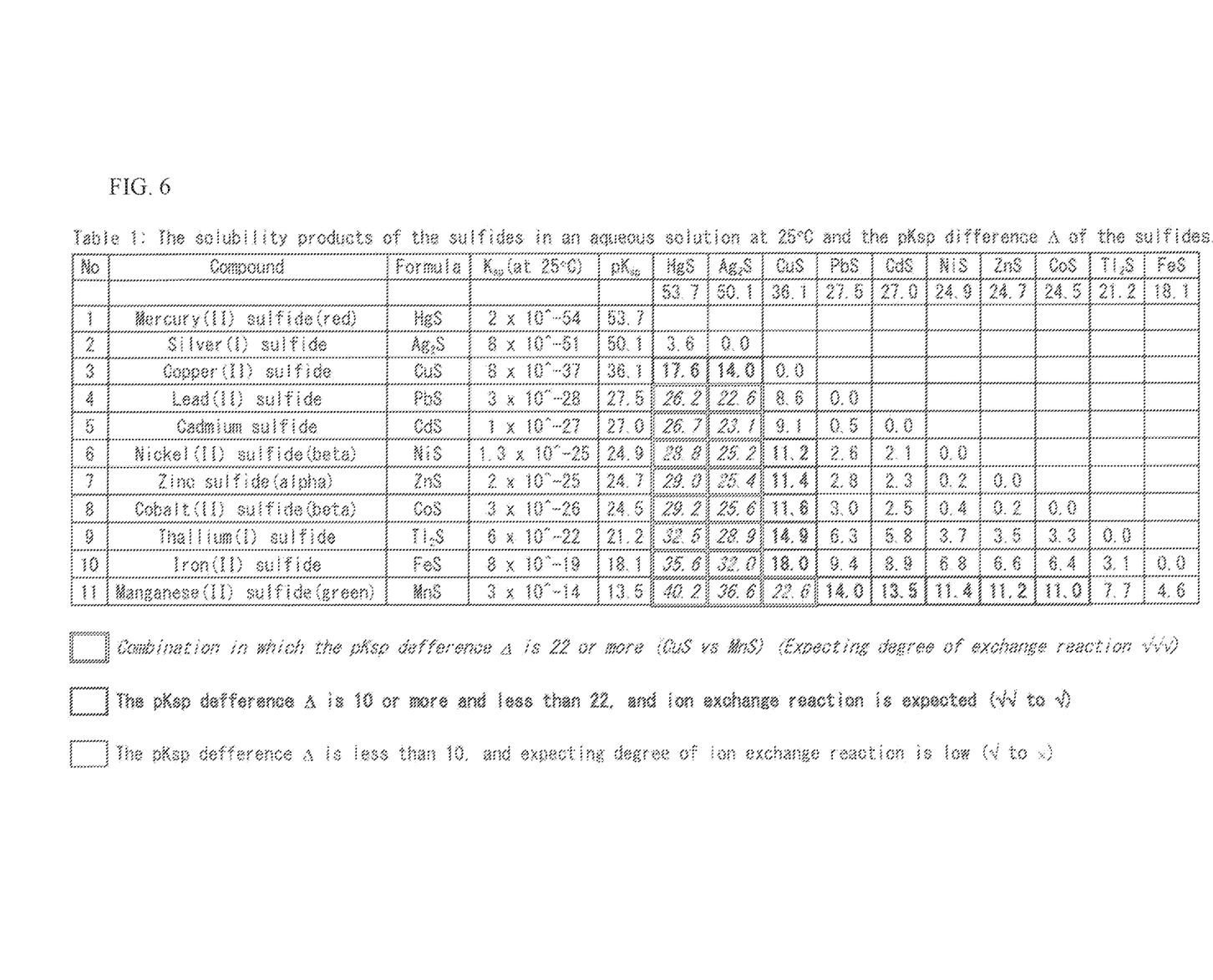
FIG. 6 is Table 1, which shows the solubility products of the sulfides in an aqueous solution at 25° C., and the pKsp difference $\Delta$ of the sulfides.

Table 1 in FIG. 6 shows the solubility products Ksp of the sulfides in an aqueous solution at 25° C., and the pKsp ($=-\log_{10}$ Ksp) difference Δ between the sulfides. In the table, the double line frame (or the dark gray frame) represents a combination of sulfides having the pKsp difference Δ of 22 or more, and it is expected that the exchange reaction easily proceeds or in units of seconds with these combinations. Expressed simply as a symbol, the expecting degree (prediction) of the exchange reaction is expressed as ✓✓✓. The thick line frame (or light gray frame) represents a combination of sulfides having the pKsp difference Δ of 10 or more and less than 22, and the exchange reaction is expected to proceed, but it may take from several minutes to several hours. Expressed simply by a symbol, the expecting degree (prediction) of the exchange reaction is expressed as ✓✓ to ✓. The thin line frame (or the white frame) represents a combination of sulfides having the pKsp difference Δ of less than 10, and it is expected that the exchange reaction hardly progresses with these combinations. Expressed simply as a symbol, the expecting degree (prediction) of the exchange reaction is expressed as ✓ to x.

Incidentally, regarding a solubility product of the sulfides, some sulfides of the same element show different solubility products depending on the crystal form and the like. In Table 1, sulfides having crystal forms and the like in which the pKsp difference Δ is small are listed. This is because even when the pKsp difference Δ of the sulfides is large, the pKsp difference Δ of the sulfides in question becomes 10 or more, and it is considered that the exchange reaction will proceed.

Although the above solubility product Ksp is a value in an aqueous solution, it is presumed that the same tendency also occurs in a nonaqueous solvent such as similar polar solvent of methanol.

For example, when MnS is present on the steel sample surface or electrolytic solution residue, the sulfide of Cu ion eluted into the electrolytic solution has a pKsp difference Δ against MnS of 22.6, so Cu ion attacks MnS. Then, Mn is ionized and expelled into the electrolytic solution, and Cu ion itself remains as CuS on the MnS surface. In other words, the inclusions and precipitates which originally existed as MnS in the Cu-containing steel sample are observed as CuS when their surface is observed. Even if mass spectrometry is performed from the residue, accurate quantification becomes impossible in the case of fine particles. It is so because CuS occupies a substantial portion of the volume of the fine particles, as CuS derived from Cu ions in the electrolytic solution exchange MnS to a thickness of about several tens of nanometers (1 to 100 nm) on the surface of MnS. The phenomenon in which such a metal near the surface is exchanged is sometimes referred to as Artifact in this specification.

Since the sulfide of Ag ion has a pKsp difference against MnS of 36.6, Ag ion attacks MnS. Then, Mn is ionized and expelled into the electrolytic solution, and Ag ion, itself remains as $Ag_2S$ on the MnS surface. This is confirmed in FIG. 5 obtained by the following procedure.

Figure 5:
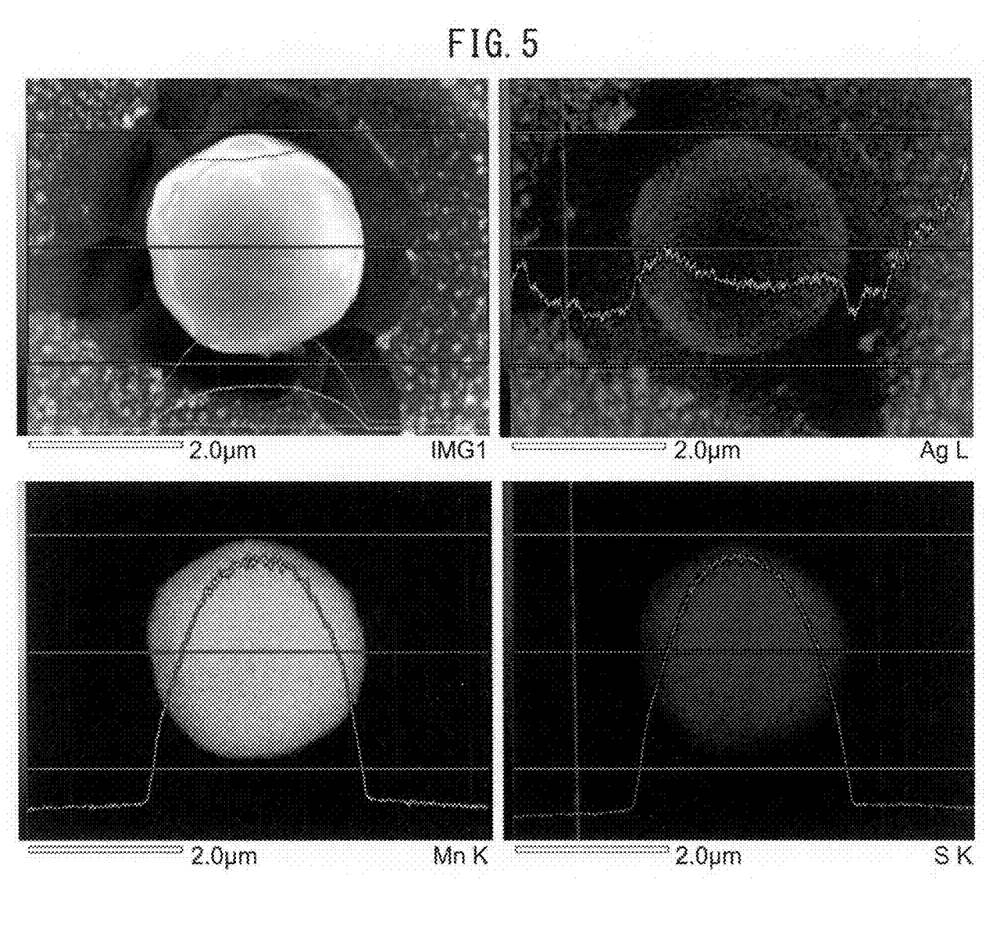
FIG. 5 is a SEM photograph and a graph showing element concentrations around inclusions of a mirror-polished steel sample.

Prepare a steel sample which has been confirmed to contain MnS as inclusions, and preliminarily mirror polish the sample in order to remove surface impurities.

Prepare an electrolytic solution (4% MS) containing 4% by mass of methyl salicylate+1% by mass of salicylic acid+1% by mass of tetramethylammonium chloride (TMAC) in methanol solvent, which is conventionally known and capable of recovering sulfide inclusions as a residue.

Carry out electrolytic dissolution of the steel sample in the electrolytic solution.

After completion of electrolytic dissolution, add a droplet of Ag ion solution into the electrolytic solution and mix it.

Observation by scanning electron microscope (SEM) and measurement of surface element concentration by EDS are performed on the steel samples which are electrolyzed on their surfaces before and after adding a droplet of Ag ion solution.

FIG. 5 shows the results after adding a droplet of Ag ion. The upper left image shows the SEM observation image, the upper right image shows the SEM observation image and the chart of the Ag concentration measured by EDS in an overlapping manner, the lower left image shows the Mn concentration chart in an overlapping manner, and the lower right image shows the S concentration chart in an overlapping manner.

Incidentally, as a matter of course, Ag was not observed before adding a droplet of Ag ion.

From the chart of each element concentration in FIG. 5, it is confirmed that only the surface portion of the MnS particle is exchanged by $Ag_2S$. Although the height (concentration) of each element in the chart is relative, the following facts can be read. Specifically, in the inclusion particle portion, the values of Mn and S in the graphs are rising as a mountain shape, and the inclusion particles contain Mn and S. Specifically, it is confirmed that the particles contain MnS as a main component. It is confirmed that the concentration of Ag is increased at the end portion of the inclusion particles and Ag is concentrated on the surface of the inclusion particles. In addition, at the central portion of the inclusion particles, the concentration of Ag does not increase and the concentrations of Mn and S are high. Therefore, it is confirmed that only the surface of MnS is exchanged by Ag.

The inventors of the present invention newly found that by using a specific electrolytic solution in the method of extracting metal compound particles in a metal material, an amount of a free attack metal in the electrolytic solution is reduced and Artifact can be prevented. The specific electrolytic solution comprises an agent which forms a complex containing a metal (attack metal) M' of the metal compound M'x'Ay', wherein a solubility product of metal compound M'x'Ay' is defined as Ksp[M'x'Ay'], and a solubility product of metal compound to be extracted MxAy, which is contained in the metal material, is defined as Ksp[MxAy], and wherein $$\Delta = pKsp[M'x'Ay'] - pKsp[MxAy] = (-\log_{10} Ksp[M'x'Ay']) - (-\log_{10} Ksp[MxAy]) \geq 10,$$

wherein M and M' are different metal elements, A is a single atom or atomic group forming a compound with M or M', and x, x', y and y' represent a composition ratio of the compound determined according to the valences of M, M' and A, and the solubility product Ksp is a value in an aqueous solution at 25° C.

Cu is remarkable as an attack metal M' which is prone to occur Artifact, due to its content and low solubility product Ksp, in other words, high pKsp. Cu easily attacks the surface of MnS or FeS having a pKsp difference Δ against the Cu compound of about 20, and can occur Artifact. However, Artifact or the attack by attack metal M' is thought to be more likely to occur as the pKsp difference Δ is larger. The object of the present invention is not limited to the combination of Cu and MnS or FeS. Specifically, the metal M' of the metal compound M'x'Ay' having a large pKsp may be at least one of Hg, Ag, Cu, Pb, Cd, Co, Zn and Ni, and it can become an attack metal M'. It is considered that the attack metal M' is mainly the one which was eluted into the electrolytic solution from the metal M' or a compound thereof contained in the steel material sample. However, the electrolytic solution or the electrolytic device is sometimes reused, and the metal M' or a compound thereof may be present in the reused electrolytic solution or electrolytic device, which may be an attack metal M'. In the electrolytic extraction operation, the metal M' or a compound thereof may be mixed in the electrolytic solution as a contamination substance and may become an attack metal M'.

M' may be at least one of Hg, Ag, Cu, Pb, Cd, Co, Zn and Ni, but is a metal element different from M. A is a single atom or atomic group forming a compound with M or M' and may comprise one or more atoms independently selected from the group consisting of C, N, H, S, O, P and F atoms. The pKsp difference Δ between sulfides of Hg, Ag, Cu, Pb, Cd, Co, Zn and Ni, and MnS, is 10 or more. In particular, the pKsp difference Δ between sulfides of Hg, Ag and Cu, and MnS, is 20 or more.

If the pKsp difference Δ between the metal compound to be extracted MxAy and the attack metal compound M'x'Ay' is about 10, Artifact can occur in several hours. An actual electrolytic extraction analysis is often carried out in the order of several hours. Therefore, combinations in which the pKsp difference Δ is about 10 may affect analysis. In the present invention, it is defined that the difference Δ of pKsp is 10 or more, and in that case, it is possible to suppress Artifact which can occur.

The larger the pKsp difference Δ between the metal compound to be extracted MxAy and the attack metal compound M'x'Ay', the easier or faster the Artifact can occur. In the present invention, a combination of MxAy and M'x'Ay' having a large pKsp difference Δ can preferably be selected, which makes it possible to suppress Artifact that can easily or quickly occur. In this respect, pKsp [M'x'Ay'] of M'x'Ay' is larger than pKsp [MxAy] of metal compound to be extracted MxAy preferably by 11 or more, more preferably by 12 or more, still more preferably by 13 or more, still more preferably by 14 or more, still more preferably by 15 or more, still more preferably by 16 or more, still more preferably by 17 or more, still more preferably by 18 or more, still more preferably by 19 or more, still more preferably by 20 or more, still more preferably by 21 or more, still more preferably by 22 or more, still more preferably by 23 or more, still more preferably by 24 or more, still more preferably by 25 or more, still more preferably by 26 or more, still more preferably by 27 or more, still more preferably by 28 or more, still more preferably by 29 or more, still more preferably by 30 or more, still more preferably by 31 or more, still more preferably by 32 or more, still more preferably by 33 or more, still more preferably by 34 or more, still more preferably by 35 or more, still more preferably by 36 or more, still more preferably by 37 or more, still more preferably by 38 or more, still more preferably by 39 or more, and still more preferably by 40 or more.

Incidentally, the solubility product Ksp is a value in an aqueous solution, but as shown in Table 2, even when a nonaqueous solvent (lower alcohol) is used, if the pKsp ($-\log_{10}$ Ksp) difference Δ obtained from Ksp is 10 or more, it has been confirmed that a reaction proceeds. Specifically, the following confirmation test was conducted.

Two kinds of steel materials containing MnS (one having a particle diameter of MnS of 1 μm or more and the other having a particle diameter of 100 to 150 nm) were prepared as samples containing an object to be extracted, and the surfaces thereof were subjected to a mirror polishing finish.

Six types of standard solution for atomic absorption analysis (M'+ solution) with a metal ion concentration of Ag, Cu, Pb, Co, Zn and Ni of 1000 μg/ml were prepared as attack metal M'+ ions, respectively. 0.1 ml of M' solution was mixed with 0.3 ml of methanol which is a nonaqueous solvent.

Mixed solution was applied to the surface of the steel material to check a change of the steel surface.

In the case of applying the mixed solution containing Ag and Cu, the color of the steel material surface was changed to black within 5 minutes from the application. In the case of applying the mixed solution containing Pb, the color of the steel material surface was changed to black in about 10 minutes from the application. In the case of applying the mixed solution containing Co, Zn and Ni, the color of the steel material surface was changed to black in about 20 minutes from the application.

In addition, SEM and EDS observations were conducted on the steel material which had discoloration, and it was confirmed that exchange of Mn and attack metal M' (that is, Artifact) occurred on the surface of MnS particles.

From this fact, it is presumed that in the scope of the present invention, the solubility product Ksp is an index in an aqueous solution, but it can also be applied to a non-aqueous solution, and the solubility product Ksp therein has the same tendency as in the aqueous solution.

It was also confirmed that the larger the pKsp difference Δ, the faster the exchange (Artifact) reaction occurs. On the other hand, it was also confirmed that, even if the pKsp difference Δ was small, the exchange (Artifact) reaction steadily progressed, although the reaction rate was relatively slow. Electrolytic extraction analysis of steel materials is often done in the order of several hours. For example, the time to immerse the sample in the electrolytic solution may be extended by about 1 hour even if it is planned in about 2 hours. Discoloration was observed in about 20 minutes when using Ni-containing solution and MnS in which the pKsp difference Δ was 10. That is, it was confirmed that the exchange (Artifact) reaction could be problematic when the pKsp difference Δ was 10 or more.

In this connection, in addition to the above confirmation test, a mixed solution of attack metal M'+ solution and methanol plus 0.1 ml of triethylenetetramine (TETA) as a complexing agent (a complexing agent additive solution) was prepared and observation was also carried out when it was applied to a mirror finished steel material. When the complexing agent additive solution was added, discoloration of the surface of the steel material was not observed even after several hours, and a good mirror polished state was maintained. Artifact was not confirmed by SEM and EDS observations.

TABLE 2 pKsp Difference Δ. Expected Occurance of Ion Exchange Reaction in Solvent and Actual Measurement Result

| pKsp Diff. Δ | 0 | 2 | 4 | 6 | 8 | 10 | 12 | 14 | 16 | 18 | 20 | 22 | 24 | 26 | 28 | 30 | 32 | 34 | 36 | 38 |
|---|---|---|---|---|---|---|---|---|---|---|---|---|---|---|---|---|---|---|---|---|
| Reaction (Expect) | x | x | ✓ | ✓ | ✓ | ✓✓ | ✓✓ | ✓✓ | ✓✓ | ✓✓ | ✓✓✓ | ✓✓✓ | ✓✓✓ | ✓✓✓ | ✓✓✓ | ✓✓✓ | ✓✓✓ | ✓✓✓ | ✓✓✓ | ✓✓✓ |
| Reaction (Actual) | | | | | | ✓Ni | ✓Zn | ✓✓Co | ✓✓Pb | | | | ✓✓✓Cu | | | | | | | ✓✓✓Ag |

Explanatory Notes: x no reaction, ✓ reaction in a long time, ✓✓ reaction in several minutes, and ✓✓✓ reaction in second unit.

A crown ether can be used as a chemical agent that forms a complex containing such an attack metal M'. A crown ether is a cyclic polyether (a series of ether units joined together) and can vary in size of the annular hole. Therefore, depending on the attack metal species M', a crown ether having an appropriate hole can be prepared, thereby only the attack metal species M' can be selectively captured.

The agent that forms a complex containing the attack metal M' may contain any one kind or two or more kinds of polyethylene amines, ethylenediamine tetraacetic acid, cyclohexanediamine tetraacetic acid. They act as a chelating agent and capture the attack metal M'. Examples of polyethyleneamines include triethylenetetramine (TETA), penicillamine, pentaethylenehexamine and the like. In particular, a chelating agent such as triethylenetetramine has a high selectivity for Cu ions, Ni ions, etc., and particularly when the attack metal M' is Cu, Ni or the like, a particularly high capturing effect is exerted.

Table 3 shows the stability constant ($Log_{10}$ Kd) of the complex when Cu or Ni as the attack metal M' is captured with various chelating agents. The higher the stability constant is, the more preferable since it is considered that it is difficult to capture and release the attack metal again. In the case of inhibiting the formation of the compound M'x'Ay', particularly CuS, as an agent that forms a complex containing the attack metal M', one having a stability constant of 10 or more, preferably of 12 or more, more preferably of 14 or more, more preferably of 16 or more, still more preferably of 18 or more, and even more preferably of 20 or more, can be selected. Generally, when a compound in which its formation is inhibited M'x'Ay' has a solubility product of Ksp [M'x'Ay'], the agent will be selected such that the difference between pKsp [M'x'Ay'](=−$Log_{10}$ Ksp [M'x'Ay']) and Log Kd, i.e., pKsp [M'x'Ay']−Log Kd is less than 26, preferably less than 24, more preferably less than 22, more preferably less than 20, still more preferably less than 18, more preferably less than 16.

TABLE 3 the stability constant (Kd) (Log value) of complex with various chelating amounts

| | Stability Constant (Log $K_d$) | |
|---|---|---|
| Chelating Agent | Cu | Ni |
| EDTA: Ethylenediaminetetraacetic acid | 18.3 | 18.2 |
| IDA: Iminodiacetic acid | 10.3 | — |
| $NH_3$ | 4.2 | — |
| EDA: Ethylenediamine | 10.7 | 7.5 |
| DETA: Diethylenetriamine | 16.1 | 10.7 |
| TETA: Triethylenetetramine | 20.4 | 14.0 |
| TEPA: Tetraethylenepentamine | 23.1 | 17.6 |
| PEHA: Pentaethylenehexamine | 26.2 | — |

The attack metal M' is captured and a complex of the attack metal M' is formed. The complex of the attack metal M' is kept dissolved in the above-mentioned solvent. Therefore, even if the metal compound MxAy having a large pKsp difference Δ is present, the attack metal M' cannot freely exchange with the metal M (that is, Artifact) on the surface of the metal compound MxAy. In other words, formation of M'x'Ay' is suppressed.

The chemical agent that forms a complex or the electrolytic solution containing the agent may be agitated in the electrolytic cell. This makes it easier for an unreacted agent to come into contact with the attack metal M', and the attack metal M' is likely to be captured. Means of stirring is not particularly limited, but bubbling by a bubble generator, vortex flow by a magnetic stirrer, or the like may be used. Alternatively, droplets of unreacted agent may be added dropwise in the vicinity of the attack metal M'. The lower limit may be 100 mL/min, preferably 200 mL/min for bubbling and 100 rpm, preferably 200 rpm for a stirrer, so that the unreacted agent can easily contact the attack metal M'. If the bubbling amount or the stirrer rotation speed is too high, problems such as delamination of the surface of the object to be electrolyzed may occur. Therefore, for bubbling, the upper limit may be 600 mL/min, preferably 500 mL/min, and for a stirrer, the upper limit may be 600 rpm, preferably 500 rpm.

Incidentally, in the general electrolytic operation, when stirring the electrolytic solution, stirring operation is performed so that the flow of the electrolytic solution generated by stirring does not come into contact with the electrolytic object. This is based on the idea that the flow of the electrolytic solution generated by stirring does not affect the electrolytic object. In the present invention, from the viewpoint that the chemical agent that forms a complex tends to come into contact with the attack metal M' or a generation source thereof, the agent may be stirred or supplied so that the flow of the electrolytic solution generated by stirring or the like comes into contact with the electrolytic object.

Further, examples of a gas for bubbling include an inert gas such as nitrogen gas, helium, argon and the like. An active gas such as oxygen or hydrogen may affect the concentration of dissolved oxygen in the electrolytic solution, which is not preferable because it may affect the electrolytic object.

The metal material in the present invention may be a steel material. The steel material refers to a material containing iron as a main component and may contain a trace amount of carbon.

When filtering the electrolytic solution after etching through a filter and extracting metal compound particles as a collected residue, the filter may be a filter made of tetrafluoroethylene resin. For identification and quantitative analysis of the inclusions or precipitates 5 and the residues 11, as a filter for collecting the inclusions or precipitates 5 and the residues 11 from the electrolytic solution, it may be difficult to use a conventional Nuclepore filter (manufactured by GE), since it is difficult for the filter to collect the residue due to dissolution damage of the filter. Especially when the chelating agent contains triethylenetetramine, the damage of the filter is remarkable. A tetrafluoroethylene resin-made filter is preferable because even when the chelating agent contains triethylenetetramine, the dissolution damage of the filter is small.

According to the present invention, it is also provided a method for analyzing metal compound particles extracted by the above method. For the metal compound particles, rough composition analysis may be performed by XRF, or detailed composition analysis may be performed by ICP. As a surface analysis method, observation by SEM, element analysis by EDS, or the like may be used. By analyzing the surface of the sample from which the metal compound is extracted during the etching, it is also possible to observe the situation in a chronological order where the metal compound is extracted.

According to the present invention, a component which can selectively retain an attack metal (Cu ion or the like) as a complex and stably hold it in the dissolved state in the electrolytic solution is added. Herein, the attack metal is a metal which attacks and exchange constituent elements of inclusions and precipitates. Accordingly, in the surface observation of the sample, it is possible to observe the inclusions and precipitates in the form originally present in the steel sample. In the identification/quantitative analysis of the inclusions and precipitates, Cu ions and the like are not incorporated into the electrolytic residue to be analyzed, and therefore, the identification and quantitative analysis accuracy of the inclusions and precipitates will not be lowered. For example, according to the surface analysis of extracted metal fine particles according to the present invention, it is no longer misidentified MnS or FeS fine particles as CuS, the true appearance (size and component) of the metal sulfide can be known. Furthermore, it is possible to accurately ascertain the content of the metal sulfide in the steel material.

It has been reported that Mn in the precipitate MnS can be readily exchanged by Se, and MnSe can be precipitated in the steel material, because it is said that MnS and MnSe have the same NaCl type structure and their lattice constants are extremely similar. From the periodic table of elements, it is expected that Te, which is the same group as S or Se, and Sb, which belongs to the adjacent group, easily exchange S of MnS and precipitates as MnTe or MnSb. If MnS is easily exchanged to form MnSe, MnTe and/or MnSb, accurate quantitative analysis of MnS is considered to be useful for improving the accuracy of quantitative analysis of MnSe, MnTe and MnSb.

Figure 7:
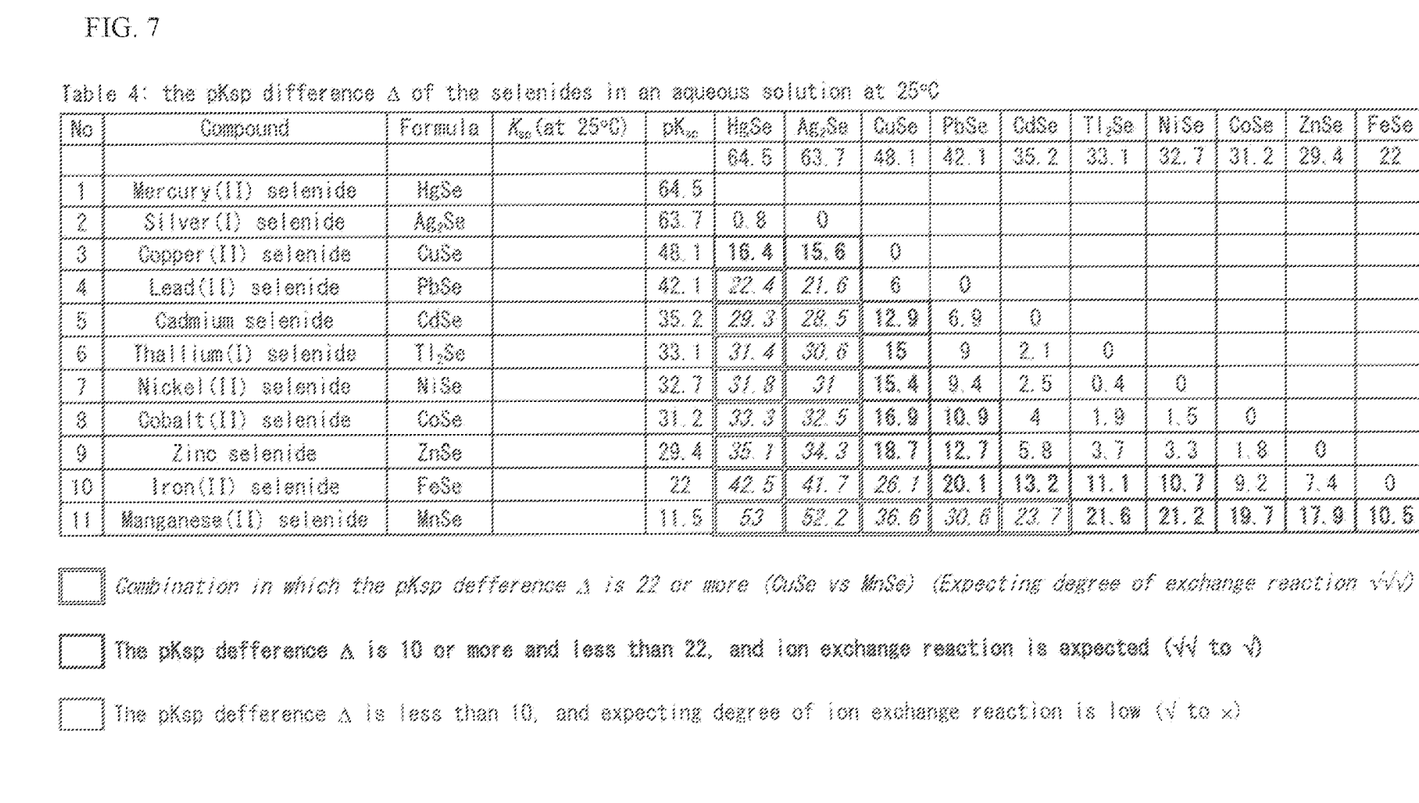
FIG. 7 is Table 4, which shows the pKsp difference $\Delta$ of the selenides in an aqueous solution at 25° C.

In addition, MnSe formed by exchange of MnS etc. can further cause an exchange (Artifact) reaction with another selenide. Table 4 of FIG. 7 shows the pKsp (=$-\log_{10}$ Ksp) difference Δ among selenides in an aqueous solution at 25° C. In the table, the double line frame (or the dark gray frame) represents a combination of selenides in which the pKsp difference Δ is 22 or more, and it is expected that the exchange reaction easily proceeds or in units of seconds with these combinations. Expressed simply as a symbol, the expecting degree (prediction) of the exchange reaction is expressed as ✓✓✓. The thick line frame (or light gray frame) represents a combination of selenides in which the pKsp difference Δ is 10 or more and less than 22, and the exchange reaction is expected to proceed, but it may take from several minutes to several hours. Expressed simply by a symbol, the expecting degree (prediction) of the exchange reaction is expressed as ✓✓ to ✓. The thin line frame (or the white frame) represents a combination of selenides having the pKsp difference Δ less than 10, and it is expected that the exchange reaction hardly progresses with these combinations. Expressed simply as a symbol, the expecting degree (prediction) of the exchange reaction is expressed as ✓ to x.

According to the present invention, it is also possible to prevent Artifact for selenide.

Furthermore, according to the present invention, there is also provided an electrolytic solution used for the above-mentioned method for extracting metal compound particles.

The electrolytic solution according to the present invention may contain a particle dispersant such as SDS, if necessary, as a component other than the agent selectively capturing the above-mentioned attack metal (Cu ion or the like) (Cu ion chelating agent or the like).

Example 1

Hereinafter, the present invention will be described by means of working examples. However, the present invention should not be construed as being limited to the following examples.

Observation of inclusions or precipitates in steel samples was carried out by the electrolytic solution and electrolytic method according to the present invention. The inclusions or precipitates of the same steel sample were observed in as the electrolyzed comparative example by using a conventional electrolytic solution (4% MS) containing 4% by mass of methyl salicylate+1% by mass of salicylic acid+1% by mass of tetramethylammonium chloride (TMAC), as a control example, which is conventionally known and capable of collecting conventionally known sulfide-based inclusions as a residue. As the electrolytic solution according to the present invention, an electrolytic solution (5% TETA) of 5% by volume of triethylenetetramine (TETA)+1% by mass of tetramethylammonium chloride (TMAC) was used. Methanol was used in either case.

Figure 2:
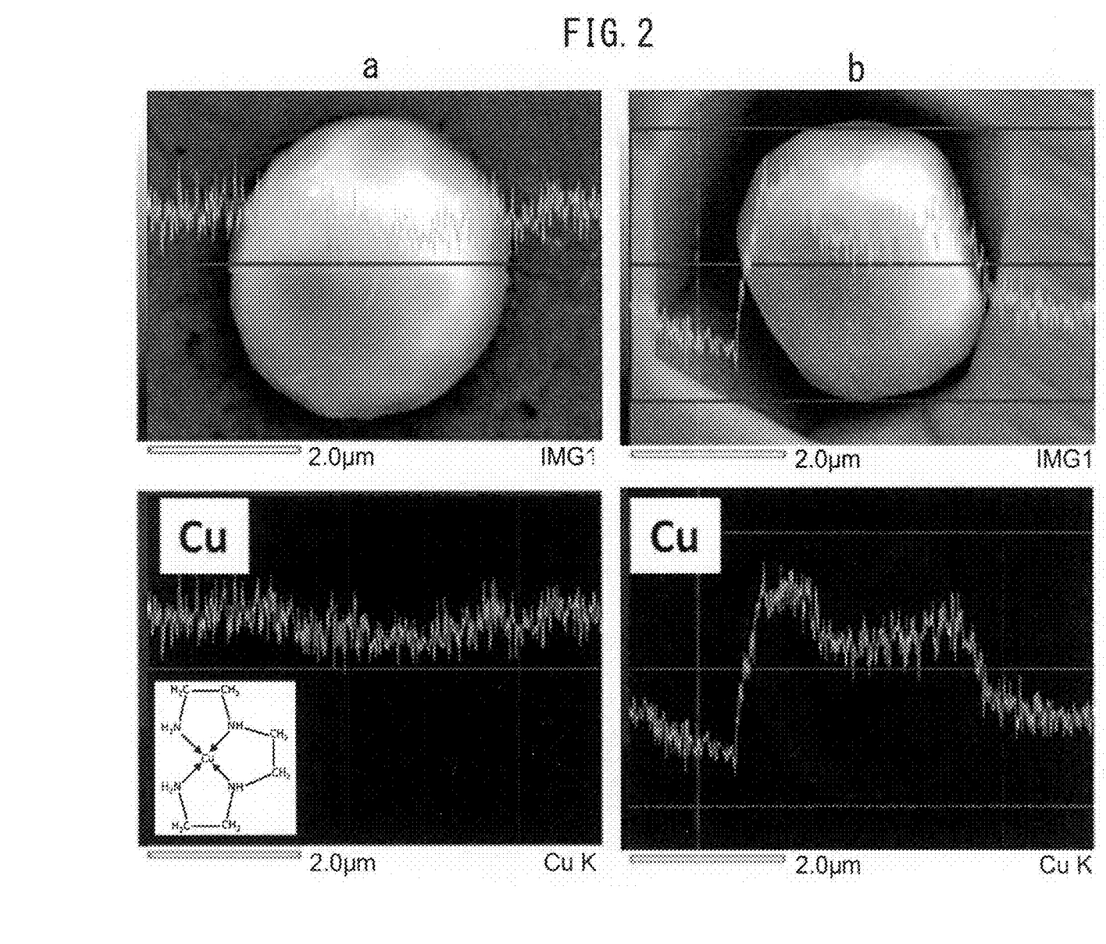
FIG. 2 is a SEM photograph and a graph showing element concentrations around inclusions of an electrochemical-polished steel sample.

The results are shown in FIG. 2.

FIG. 2a is an observation photograph by scanning electron microscope of a steel sample obtained by electrolyzing its surface with the electrolytic solution according to the present invention, and FIG. 2b is an observation photograph by scanning electron microscope of a steel sample obtained by electrolyzing its surface with a conventional electrolytic solution, on which a graph showing the Cu concentration measured by EDS was superimposed, respectively. Prior to electrolytic dissolution, the steel sample was preliminarily mirror-polished in order to remove surface impurities.

Under each scanning electron microscope photograph, only Cu concentration graphs were extracted and shown.

Since the height (Cu concentration) in the graph is a relative value, it can be seen that there is no difference in Cu concentration between the precipitated particle and the Fe matrix portion, when electrolyzing with the electrolytic solution according to the present invention. On the other hand, when the Cu concentration is measured after electrolyzing with the conventional electrolytic solution shown in FIG. 2b, it can be seen that the Cu concentration is increased in the precipitated particle portion.

With respect to the steel samples used in the above example and comparative example, the inventors carried out only mirror polishing for an elemental analysis.

Figure 3:
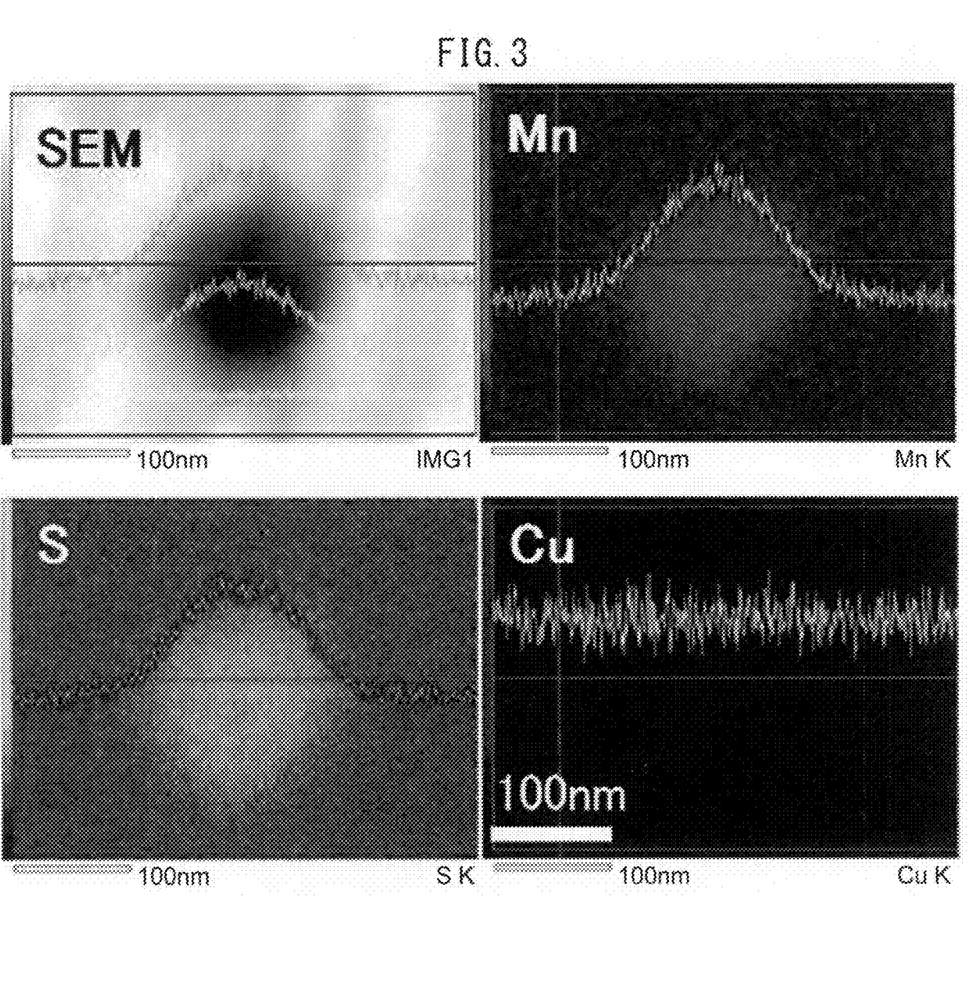
FIG. 3 is a SEM photograph and a graph showing element concentrations around inclusions of a mirror-polished steel sample.

The results are shown in FIG. 3. In the figure, SEM is a scanning electron micrograph of a portion where inclusion particles exist. Elemental analysis was performed on this particle and its vicinity.

As a result, it was confirmed that the values of Mn and S in the graphs increased at the inclusion particle portion, and thus the inclusion particles contained Mn and S, i.e., specifically MnS.

On the other hand, no peak of the Cu component was observed, and it was also confirmed that the Cu component was not included in the inclusions.

From the above results, it was confirmed that, when a steel sample was electrolyzed using a conventional electrolytic solution and observation by SEM etc. and microanalysis by EDS were performed, there was a problem that MnS which should have originally been observed in the steel material was observed as CuS, since the sample was immersed in the electrolytic solution, and at least the surface of MnS was contaminated with CuS.

On the other hand, if the electrolytic solution according to the present invention is used, since MnS is retained as MnS without causing the above-mentioned problem, observation by SEM or the like and microscopic analysis by EDS can be carried out in the state originally present in the steel sample. Therefore, the great improvement of the analysis accuracy of steel samples can be achieved.

Example 2

Quantitative analysis of the inclusions or precipitation phases in steel samples was carried out by electrolytic dissolution using the electrolytic solution according to the present invention. As a control example, a comparative example electrolyzed using a conventional electrolytic solution was prepared.

In this example, a steel material containing 0.4% by mass of Cu was solutionized by heat treatment at 1350° C. for 30 min and then rapidly cooled in water, and the resulting material was used as a steel sample.

The following three kinds of electrolytic solutions were prepared.

(1) 4% MS: 4% by mass of methyl salicylate+1% by mass of salicylic acid+1% by mass of tetramethylammonium chloride (TMAC) which is conventionally known and can recover sulfide type inclusions as a residue as a control example.

(2) 4% MS+5% TETA: 4% MS described in (1) to which 5% by volume of triethylenetetramine (TETA) capable of forming a complex with Cu ion is added.

(3) 5% TETA:Electrolytic solution having 5% by volume of triethylenetetramine (TETA)+1% by mass of tetramethylammonium chloride (TMAC).

It is noted that methanol was used as a solvent in any of (1) to (3).

For each electrolytic solution, about 1 g of the sample was electrolyzed, and the contents of Mn and Cu contained in the obtained electrolytic residue were quantified by wet chemical analysis, and their contents contained in the 1 g steel sample was calculated.

Figure 4:
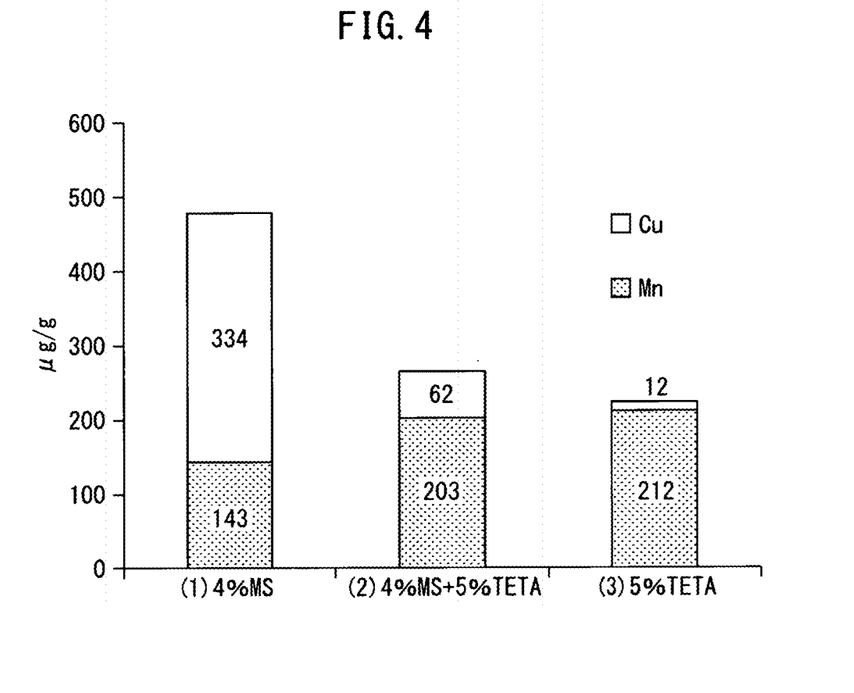
FIG. 4 is a graph showing an analysis result of an electrolytic residue of a steel sample.

The results are shown in FIG. 4.

In the figure, the three band graphs show Mn and Cu detected from the electrolytic residue in % units, respectively. From the left side, (1) the case where the sample was electrolyzed in the conventional electrolytic solution (4% MS) (2) the case where the sample was electrolyzed in the electrolytic solution according to the present invention comprising 5% by volume of TETA in addition to the conventional electrolytic solution (4% MS+5% TETA), and (3) the case where the sample was electrolyzed in the electrolytic solution according to the present invention comprising 5% by volume of TETA (5% TETA) were shown. In each case, electrolytic dissolution was performed using Pt electrode as a cathode.

When the steel samples adopted in the examples were mirror polished and the distribution of its component elements was analyzed by EDS or the like, it was confirmed that the Cu contained in the sample was mostly solid-solved in the sample matrix portion, and was not present in sulfide form such as CuS and $Cu_2S$.

Nonetheless, in the electrolytic dissolution with the conventional electrolytic solution (4% MS) shown in (1) of FIG. 4, Cu concentration (334 ppm) which is higher than Mn concentration (143 ppm) was measured from the electrolytic residue whose main component is sulfide in the steel sample.

The graph shown in (2) shows the concentrations of Mn and Cu measured from the electrolytic residue when electrolyzed with the electrolytic solution according to the present invention, where 5% by volume of triethylenetetramine was added (4% MS+5% TETA).

In this case, the Cu component in the electrolytic residue was decreased to 62 ppm.

In addition, (3) shows measured values in the case of the electrolyte solution of 5% by volume of triethylenetetramine electrolytic solution according to the present invention (5% TETA).

The Cu concentration measured from the electrolytic residue was decreased to 12 ppm.

Incidentally, in the electrolytic solution according to the present invention wherein triethylenetetramine is added to the electrolytic solution, the conventional Nuclepore filter would be dissolved. Therefore, it is necessary to use a filter which is insoluble in the electrolytic solution.

The inventors of the present invention have discovered that by using a polyfluoroethylene filter, it is possible to prevent the dissolution phenomenon of the filter.

That is, by electrolyzing a steel sample using the electrolytic solution according to the present invention, the chemical analysis accuracy of the residue is improved, and inclusions and precipitates present in the sample can be accurately identified and quantified.

INDUSTRIAL APPLICABILITY

By electrolyzing a steel sample using an electrolytic solution according to the present invention, it becomes possible to observe inclusions and precipitates in the sample in the form originally present in the sample. Further, in chemical analysis of the inclusions and precipitates, contamination due to incorporation of Cu etc. can be eliminated, and the accuracy of chemical analysis can be improved.

REFERENCE SIGNS LIST 4 metal sample
5 inclusions and precipitate grains
6 electrode (cathode side)
7 reference electrode
8 power supply (potentiostat)
9 electrolytic solution
10 electrolytic cell
11 electrolytic residue

The invention claimed is:

1. An electrolytic solution for extracting metal compound particles in a metal material by etching the metal material, wherein the electrolytic solution comprises a nonaqueous solvent, a metal compound $M'x'Ay'$, a metal compound to be extracted MxAy, and a chemical agent that forms a complex containing metal M', wherein the chemical agent comprises at least one of a crown ether, a polyethylene amine, ethylenediamine tetraacetic acid and cyclohexanediamine tetraacetic acid, and the nonaqueous solvent comprises at least one of methanol, ethanol and isopropyl alcohol, wherein a value Δ defined by the following formula is 10 or more $$\Delta = pKsp[M'x'Ay'] - pKsp[MxAy] = (-\log 10\ Ksp[M'x'Ay']) - (-\log 10\ Ksp[MxAy])$$

wherein Ksp[M'x'Ay'] represents a solubility product of metal compound M'x'Ay' and Ksp[MxAy] represents a solubility product of the metal compound to be extracted MxAy, which is contained in the metal material, wherein M and M' are different metal elements, A consists of one or more of C, N, H, S, Se, Te, O, P and F for forming a compound with M or M', and x, x', y and y' represent a composition ratio of compound determined according to the valence of M, M' and A, and the solubility product Ksp is a value in an aqueous solution at 25° C., and wherein the metal compound to be extracted MxAy is one or more of MnS, FeS, MnSe or FeSe.

2. The electrolytic solution according to claim 1, wherein the metal compound to be extracted MxAy is one or two of MnS or FeS.

3. The electrolytic solution according to claim 1, wherein the metal M' of the metal compound M'x'Ay' whose solubility product Ksp is smaller, is at least one of Hg, Ag, Cu, Pb, Cd, Co, Zn and Ni.

4. The electrolytic solution according to claim 1, wherein the chemical agent comprises a crown ether.

5. The electrolytic solution according to claim 1, wherein the chemical agent comprises any one kind or two or more kinds of polyethylene amines, ethylenediamine tetraacetic acid, cyclohexanediamine tetraacetic acid.

6. The electrolytic solution according to claim 5, wherein the chemical agent comprises triethylenetetramine.

7. The electrolytic solution according to claim 1, wherein the metal material is a steel material.

8. The electrolytic solution according to claim 1, wherein the metal compound to be extracted MxAy is one or two of MnS or FeS;

the metal M' of the metal compound M'x'Ay' whose solubility product Ksp is smaller, is at least one of Hg, Ag, Cu, Pb, Cd, Co, Zn and Ni;

the chemical agent comprises any one kind or two or more kinds of polyethylene amines, ethylenediamine tetraacetic acid, cyclohexanediamine tetraacetic acid; and the nonaqueous solvent contains at least one of methanol and ethanol.

9. An electrolytic solution for extracting metal compound particles in a metal material by etching the metal material, wherein the electrolytic solution consists essentially of a nonaqueous solvent, a metal compound M'x'Ay', a metal compound to be extracted MxAy, and a chemical agent that forms a complex containing metal M', wherein the chemical agent is selected from the group consisting of at least one of a crown ether, a polyethylene amine, ethylenediamine tetraacetic acid and cyclohexanediamine tetraacetic acid, and the nonaqueous solvent consists of at least one of methanol, ethanol and isopropyl alcohol, wherein a value Δ defined by the following formula is 10 or more $$\Delta = pKsp[M'x'Ay'] - pKsp[MxAy] = (-\log 10\ Ksp[M'x'Ay']) - (-\log 10\ Ksp[MxAy])$$

wherein Ksp[M'x'Ay'] represents a solubility product of metal compound M'x'Ay' and Ksp[MxAy] represents a solubility product of the metal compound to be extracted MxAy, which is contained in the metal material, wherein M and M' are different metal elements, A consists of one or more of C, N, H, S, Se, Te, O, P and F for forming a compound with M or M', and x, x', y and y' represent a composition ratio of compound determined according to the valence of M, M' and A, and the solubility product Ksp is a value in an aqueous solution at 25° C., and wherein the metal compound to be extracted MxAy is one or more of MnS, FeS, MnSe or FeSe.

* * * * *